United States Patent [19]

Edwards et al.

[11] Patent Number: 4,931,569
[45] Date of Patent: Jun. 5, 1990

[54] PURIFICATION OF STABLE WATER-SOLUBLE DIOXETANES

[75] Inventors: Brooks Edwards; John C. Voyta, both of Cambridge, Mass.

[73] Assignee: Tropix, Inc., Bedford, Mass.

[21] Appl. No.: 244,006

[22] Filed: Sep. 14, 1988

[51] Int. Cl.$^5$ .................... C07D 321/00; C07F 9/12
[52] U.S. Cl. .................................. 549/221; 549/332; 549/510; 549/511
[58] Field of Search ............... 549/221, 332, 510, 511

[56] References Cited

FOREIGN PATENT DOCUMENTS 87108978 6/1987 European Pat. Off. .

OTHER PUBLICATIONS

Adam et al., J. Org. Chem. 49:3920 (1984).
Schaap et al., Tetrahedron Letts. 28:935 (1987).
Hummelen et al., Meth. Enzymol. 133:531 (1986).
Schaap et al., J. Am. Chem. Soc. 104:3504 (1982).
Baumstark et al., J. Org. Chem. 48:3713 (1983).
Jefford et al., J. Chromat. 347:183 (1985).

Primary Examiner—Richard L. Raymond
Attorney, Agent, or Firm—Lyon & Lyon

[57] ABSTRACT

Methods are disclosed for purifying chemiluminescent water-soluble 1,2-dioxetane derivatives suitable for use as reporter molecules in a variety of biological analytical systems, including enzyme-linked immunoassays, nucleic acid probe techniques, and structural determinations. The methods are based upon high pressure, medium pressure or low pressure liquid chromatography using as the stationary phase alkaline pH-stable compositions with the chromatographic characteristics of reversed-phase adsorbents, at alkaline pH values, and in the absence of acid-forming compounds or compounds with an unshared pair of electrons. Desalting of substantially pure water soluble 1,2-dioxetane derivatives may be accomplished by the same chromatographic systems or by molecular sieve chromatography systems, but in the absence of salt buffers. Under some circumstances, purification and desalting may be combined in a single chromatographic step. Substantially pure chemiluminescent water-soluble 1,2-dioxetane derivatives prepared by the methods of the invention are also disclosed.

31 Claims, 12 Drawing Sheets

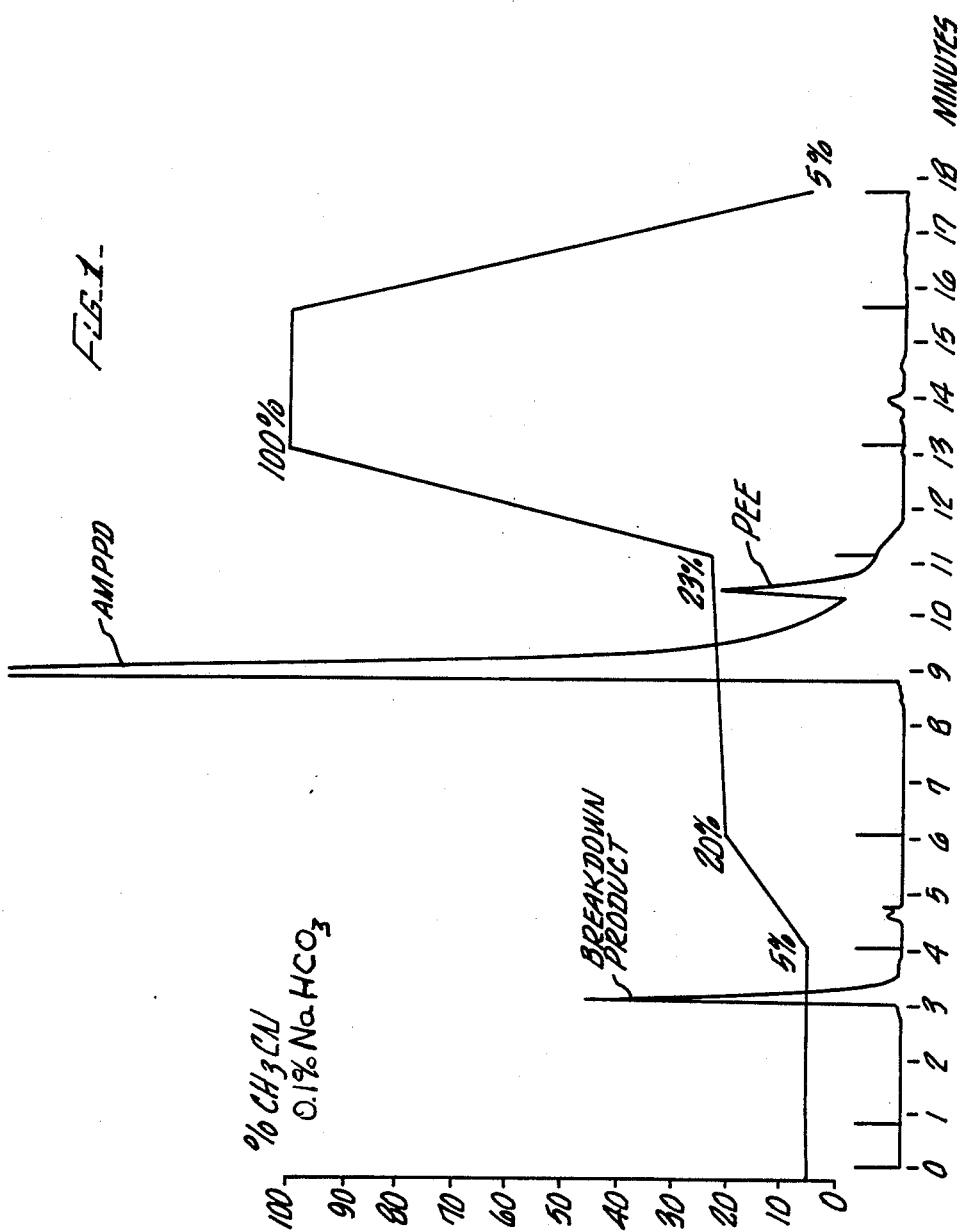

FIG_2
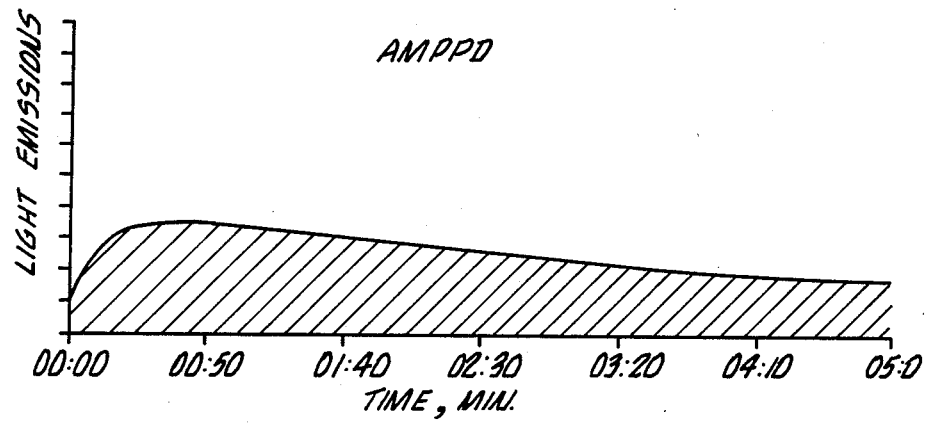
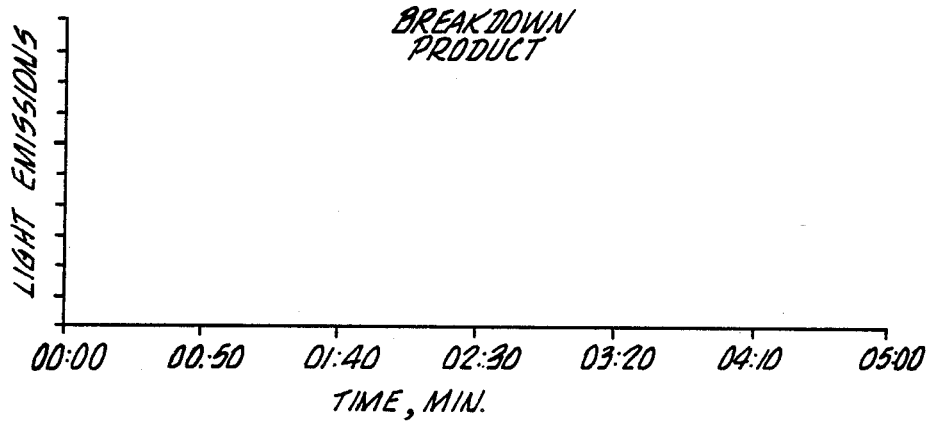

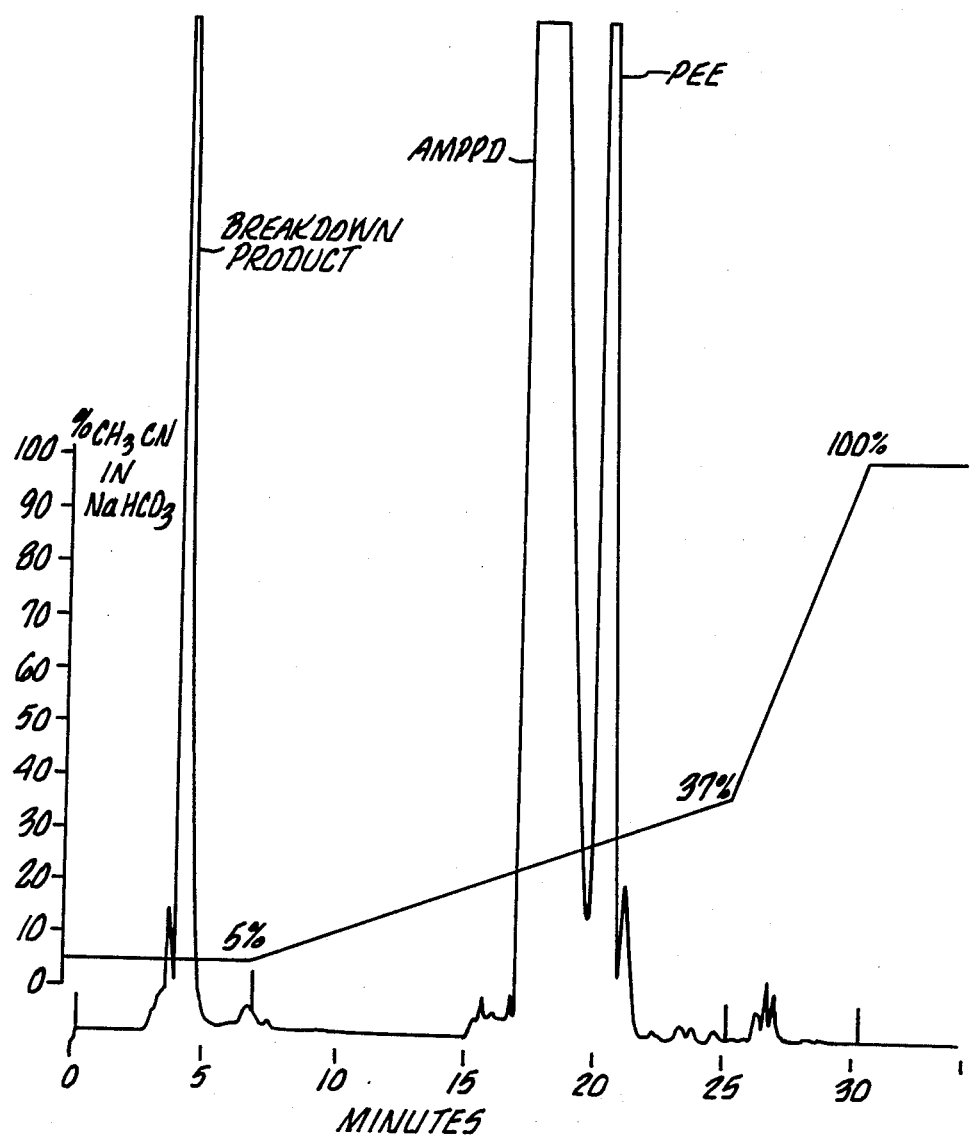

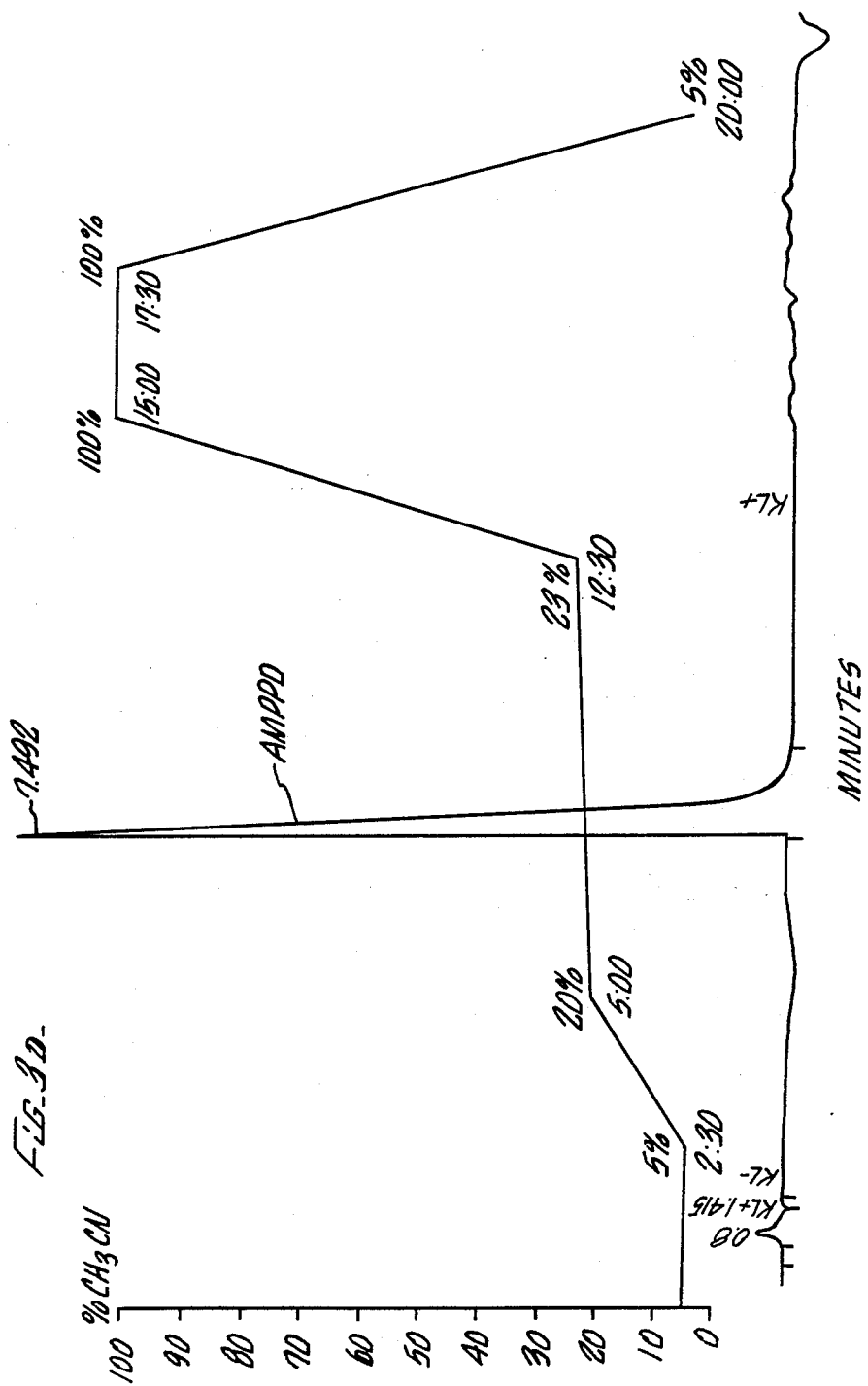

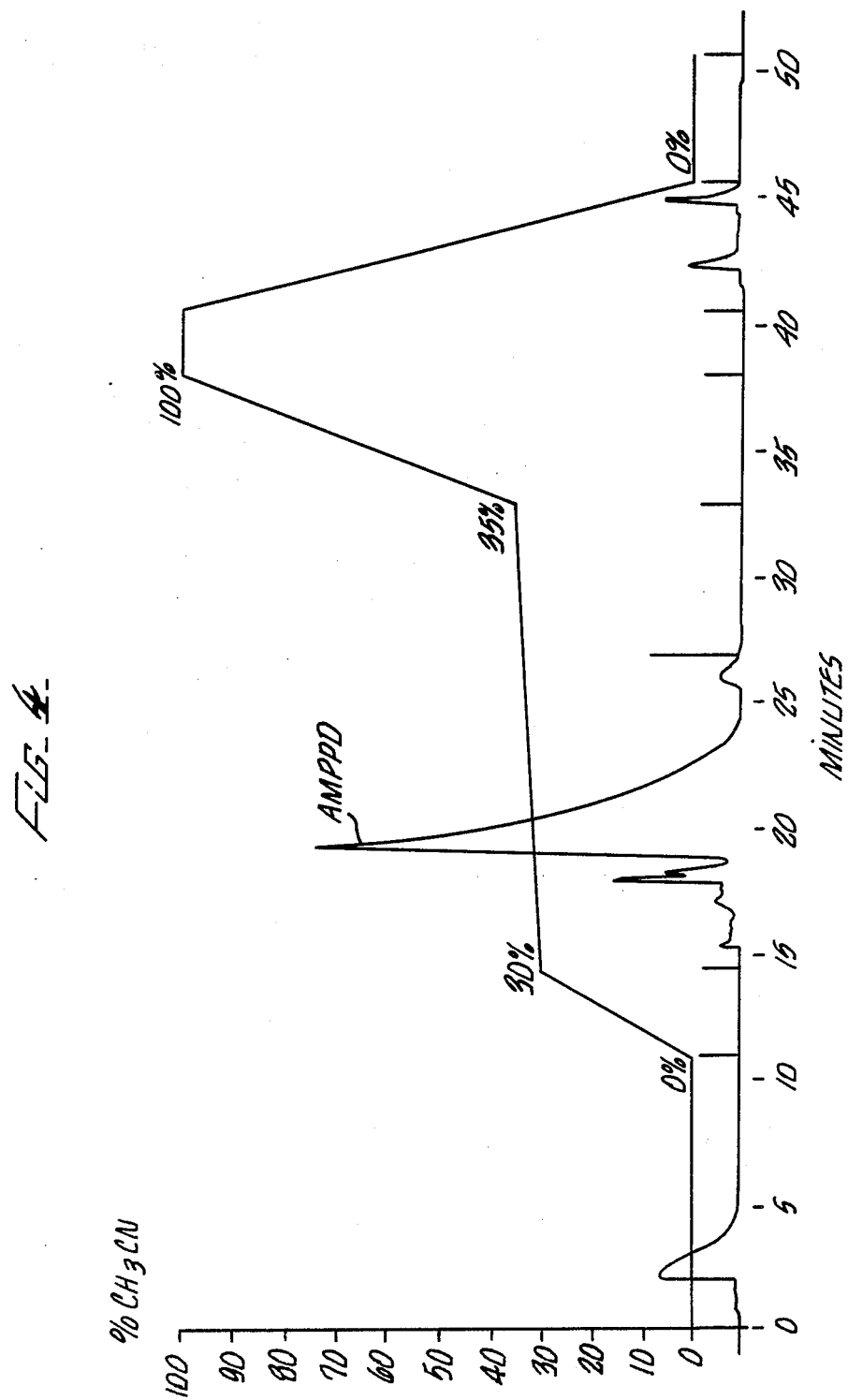

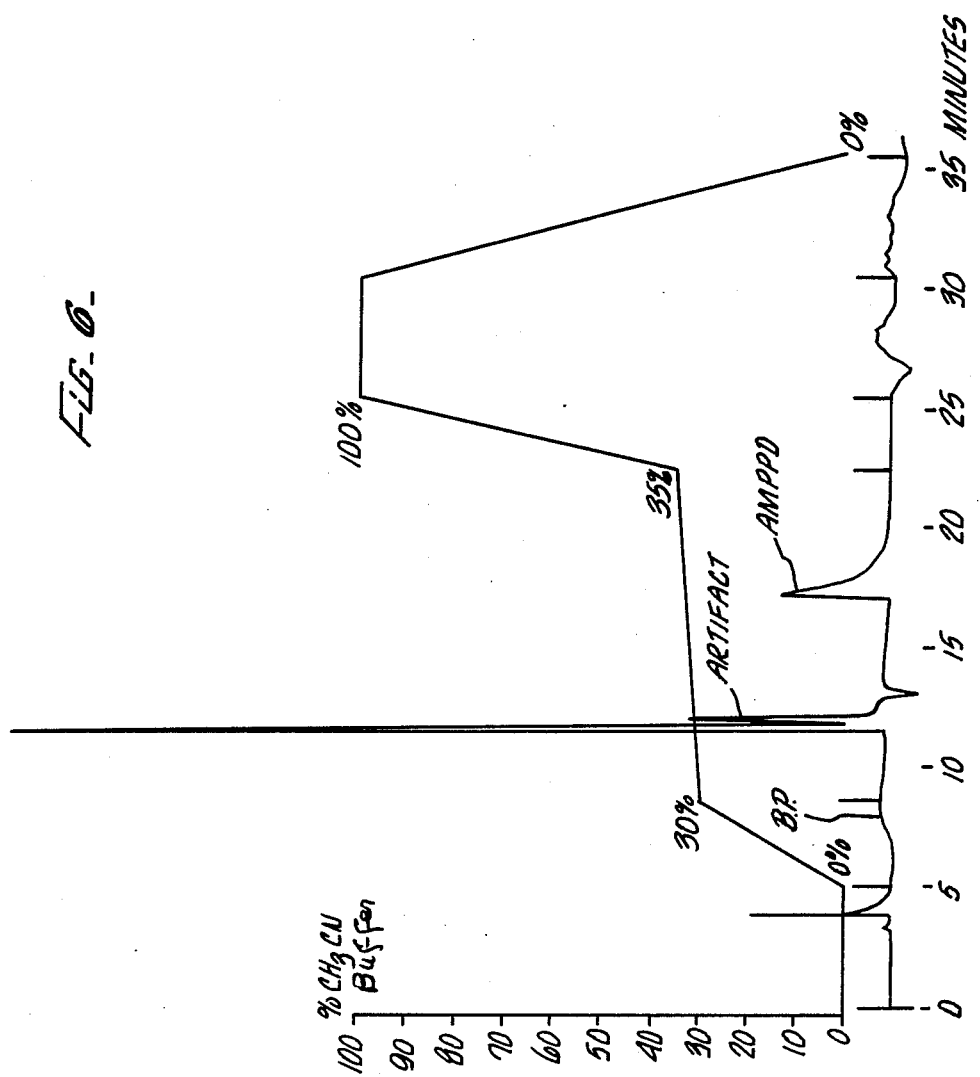

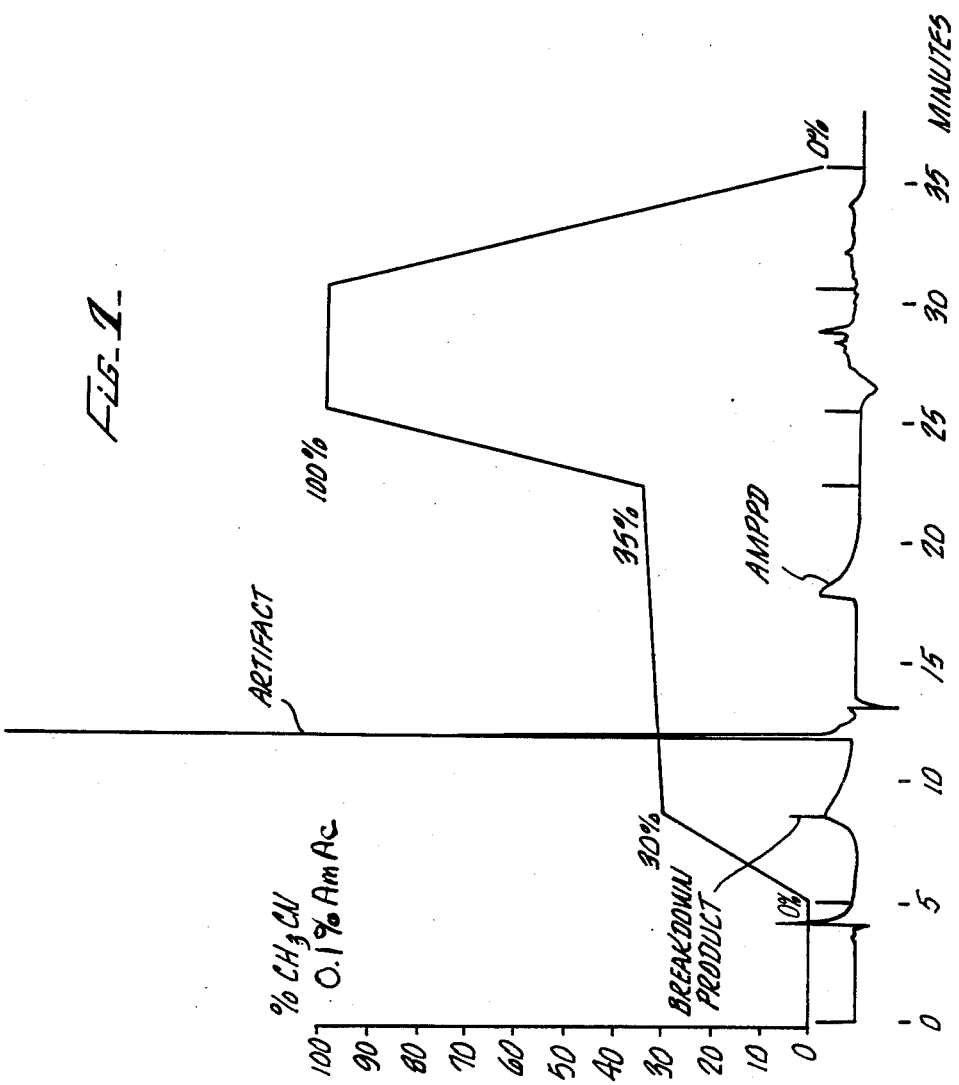

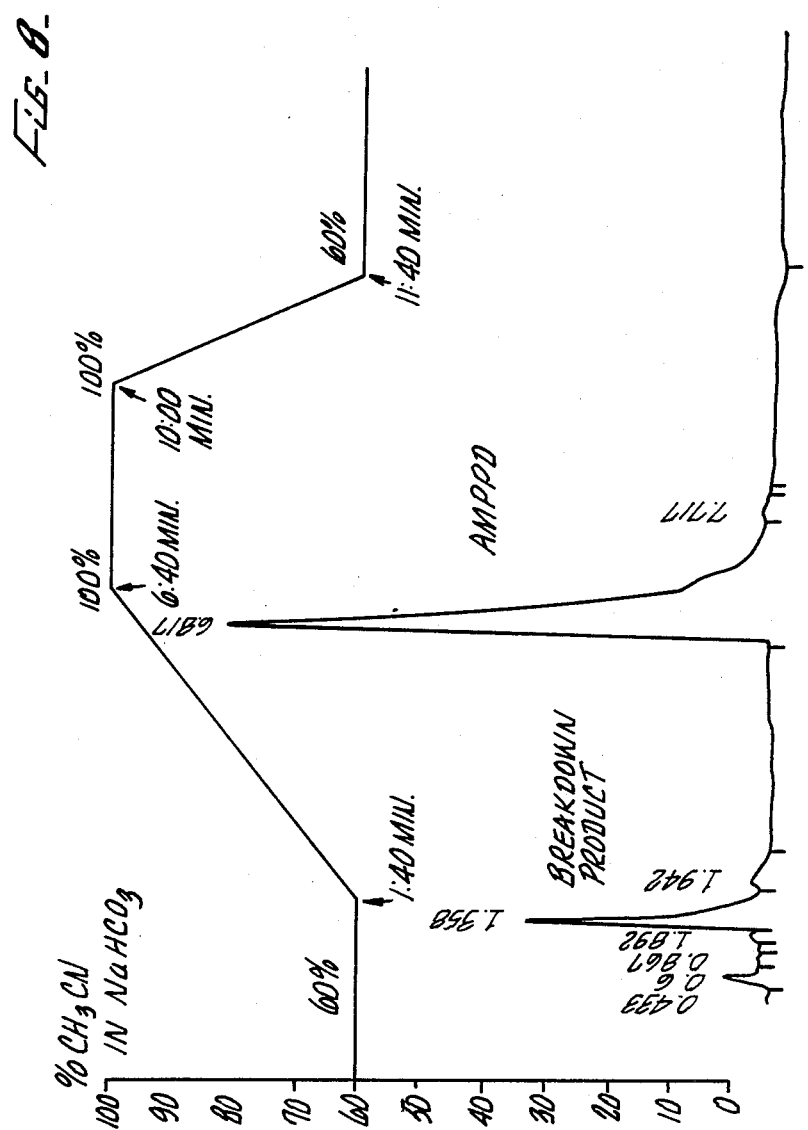

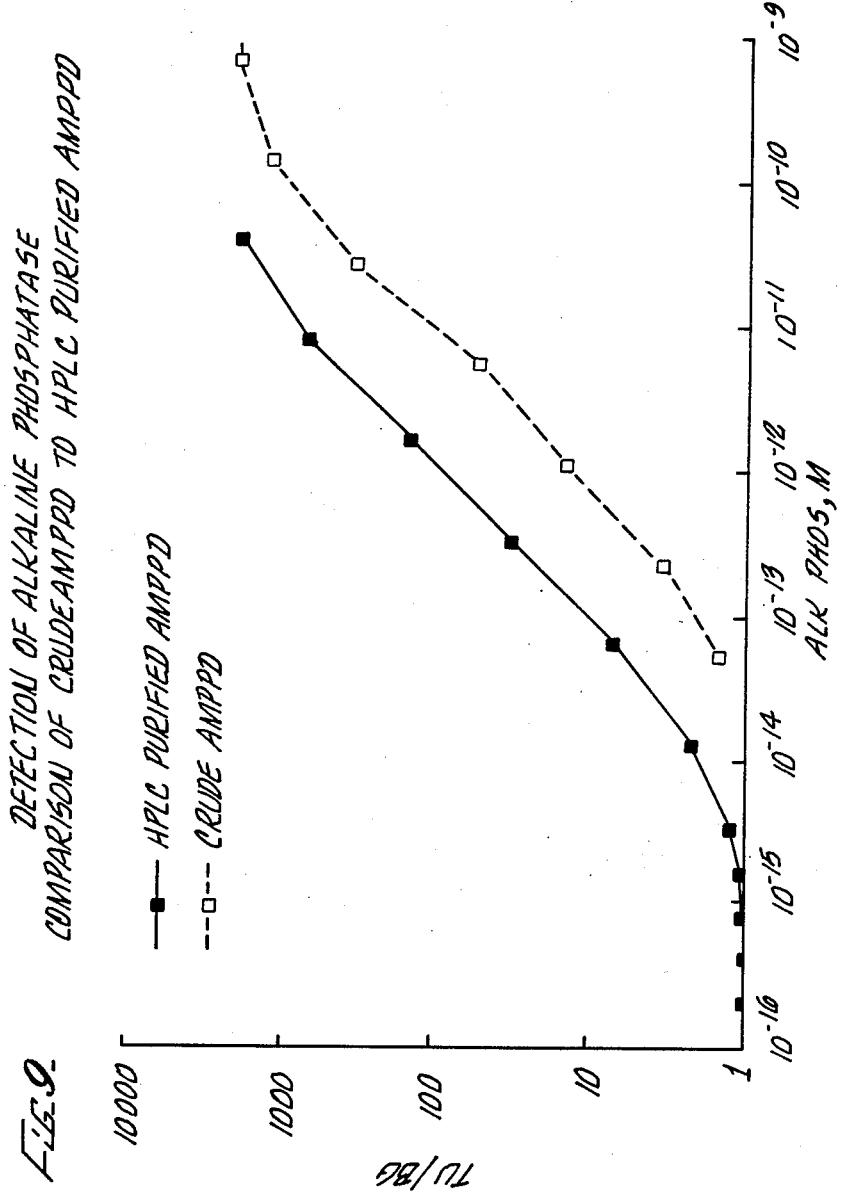

PURIFICATION OF STABLE WATER-SOLUBLE DIOXETANES

FIELD OF THE INVENTION

This invention relates to improvements in the purification of water-soluble derivatives of chemiluminescent 1,2-dioxetanes that are capable of releasing electromagnetic, including optically detectable energy, as a result of their decomposition in aqueous media. More particularly, this invention relates to improved purification of chemiluminescent 1,2-dioxetane derivatives used to determine the presence, concentration or structure of a substance in an aqueous sample, particularly when such chemiluminescent compounds are of a type used for qualitative and quantitative determination of chemical of biochemical substances by art-recognized immunoassay techniques, chemical assays or nucleic acid probes, or when they are used as direct physical or chemical probes for studying the molecular structure or microstructure of various molecules, such as synthetic polymers, proteins, glycoproteins, phosphorylated proteins, nucleic acids and the like.

BACKGROUND OF THE INVENTION

The decomposition of chemiluminescent chemical compounds to release electromagnetic, and especially optically detectable, energy—usually luminescence in the form of visible light—is well known and understood. The incorporation of such light emitting reactants in art-recognized immunoassays, chemical assays, nucleic acid probe assays, and physical and chemical probe techniques as a means by which the analyte, a substance whose presence, amount or structure is to be determined, is actually identified or quantified, has assumed increasing importance in recent years, particularly with the advent of enzymatically-cleavable water-soluble 1,2-dioxetanes. See, for example, copending Bronstein U.S. Pat. Ser. No. 889,823, "Method of Detecting A Substance Using Enzymatically-Induced Decomposition of Dioxetanes", filed July 24, 1986; Bronstein et al. U.S. patent application Ser. No. 140,035, "Dioxetanes For Use In Assays", filed Dec. 31, 1987; Edwards et al. U.S. patent application Ser. No. 140,197, "Synthesis of 1,2-Dioxetanes and Intermediates Therefore", filed Dec. 31, 1987 now abandoned; and Voyta et al. U.S. patent application Ser. No. 286,725 "Chemiluminescence Enhancement", filed June 1, 1988.

When these chemiluminescent 1,2-dioxetane derivatives are used to analyze and study substances in biological systems, and as biological systems are aqueous, the chemiluminescent compound or compounds used should be soluble in a polar protic environment, especially in aqueous media. Thus, the present invention particularly relates to the purification of chemiluminescent 1,2-dioxetane derivatives that (1) can be induced to decompose to yield a moiety in an excited state, such moiety having a heteropolar character that makes it susceptible to environmental effects, and that (2) are usable to determine the presence, concentration or structure of a substance in a polar protic environment, particularly a substance in an aqueous sample.

The prior art methods for purification of dioxetanes of which applicants are aware were designed for dioxetanes that are soluble only in organic solvents. Thus, Adam et al., J. Org. Chem. 49:3920 (1984), carried out the synthesis of aryl-substituted 1,2,dioxetanes in methylene chloride, evaporated the solvent at reduced pressure, chromatographed the residue on silica gel in a mobile phase consisting of 4:1 petroleum ether:methylene chloride at low temperatures, then recrystallized the product from organic solvents. Schaap et al., *Tetrahedron Letters*, 28:935 (1987), carried out the synthesis of adamantyl methoxy naphthyl 1,2-dioxetane in methylene chloride, evaporated the solvent in vacuo, and then recrystallized the dioxetane from pentane/ether. Hummelen et al., *Methods In Enzymology*, 133:531 (1986), synthesized a series of compounds based on adamantylidene adamantane 1,2-dioxetane in organic solvents and, after removal of the solvents in vacuo, used the compounds without further purification. Also using dioxetane products without further purification were Schaap et al., *J. Amer. Chem. Soc.*, 104:3504 (1982), who carried out the synthesis of phenol-substituted 1,2-dioxetanes in acetone solvent and then simply evaporated the solvent in vacuo to give an oily product. Schaap in published European Patent Application No. EP 87108978 discloses purifying water-insoluble derivatives of 1,2-dioxetanes by preparative thin layer chromatography in organic solvents, and by recrystallization at $-25°$ C. in hexane or pentane. Although a water-soluble dioxetane, namely, a phosphorylated xanthone derivative, is discussed in this published European application, this compound was synthesized and used without any reported purification. Baumstark et al., *J. Org. Chem.* 48:3713 (1983), purified 3-methyl-3-ethyl-1,2-dioxetanes in carbon tetrachloride on a silica gel column in pentane at $-30°$ C.

Water-soluble arylphosphate compounds other than phosphorylated 1,2-dioxetanes or analogous enzymatically, chemically or thermally cleavable chemiluminescent compounds have been purified by recrystallization. For example, 4-methylumbelliferyl phosphate was recrystallized from ethanol/diethyl ether in low yield (Fernlay, H., et al. *Biochem. J.* 97:95 (1965)). Although barium salts or salts with organic bases such as cyclohexylamine are often used to enhance the crystallinity of organic phosphate molecules (Reese, C. B., et al., *J. Chem. Soc.* (C) 2092 (1970)), dioxetanes, whether phosphorylated or not, and amines are incompatible [Lee, D. C-S. et al. in "Chemiluminescence and Bioluminescence", eds. Cormier, M. J. et al. (New York: Plenum Publishing Corp., 1973,) p. 265)]. ($-$)-5-Enolpyruvylshikimate-3-phosphate. $Na_4+$ was successfully purified by ion exchange chromatography using a triethylammonium bicarbonate buffer gradient (Chouinard, et al. *J. Org. Chem.* 51:76 (1986)). As noted above, however, dioxetanes, being sensitive to amine-catalyzed degradation are unstable in the presence of an amine base (see Examples below).

The marked instability of dioxetanes in low pH media has been noted repeatedly (see, for example, Bartlett, P. D, *Chem. Soc. Reviews* 5:149 (1976). Acidity produced by solid phases, e.g., silica gel, and the low pKa of alcoholic solvents are also known to decompose dioxetanes (see, for example, Zaklika, K. A. *Photochem. Photobiol.* 30:35 (1979), and McCapra, F., et al., *JCS Chem. Commun.* 944 and 946 (1977).

The destructive effect of acidity or amines on dioxetanes means, unfortunately, that the most useful of the buffer salts customarily used in liquid chromatography —ammonium salts (i.e., ammonium acetate or ammonium carbonate) —cannot be used to purify water soluble dioxetanes by this method. In traditional purification schemes in which such salts can be used, they will customarily be added in amounts sufficient to put them in equilibrium with amine and acid components which are volatile in high vacuum, even at the low temperatures at which such procedures are usually carried out. This is important as it provides a simple means of removing these buffer salts during the isolation of water-soluble compounds: removal of the solvent and the buffer salt in vacuo. If, however, one attempts to use ammonium salts as buffers when purifying dioxetanes the acidic moiety produced during evaporation produces a pH that will, as the concentration of the acidic moiety increases, in turn decompose the water soluble dioxetane one is trying to purify.

High performance liquid chromatography (HPLC), also known as high pressure liquid chromatography, has been used to study the thermal stability of several water-insoluble tricyclodecane spiro phenoxy 1,2-dioxetanes following purification of these compounds by recrystallization from hexane at −78° C. [Jefford, C. W., et al. *J. Chromat.* 347:183-7 (1985)]. Although the dioxetanes did not decompose during HPLC on a Li-Chrosorb Si60 column, it is important to note that, because of the water-insolubility of the dioxetanes separated, HPLC had to be performed with organic solvents, that is, the dioxetanes were injected onto the column in o-xylene solution, and isoctane-tetrahydrofuran mixtures were used as the mobile phase. Such systems cannot be used to purify water-soluble chemiluminescent 1,2-dioxetene derivatives such as those used in aqueous analytical systems.

In silica columns for liquid chromatography, at pH values at or above 7.5 where dioxetanes are stable, the silica packing is unstable and dissolves, as shown by the data in the Waters Associates, Inc. Manual of Liquid Chromatography (1988).
Contrariwise, at acidic pH values, at which silica columns are most stable, dioxetanes are unstable (Zaklika et al. supra).

To sum up, then, the purification of water-soluble dioxetanes cannot be accomplished satisfactorily (i.e., without decomposing the dioxetane one is attempting to purify) in low pH media, whether buffered or not, using either conventional HPLC or medium pressure liquid chromatography (MPLC) systems in which a silica- or crosslinked polymer-based reversed phase adsorbent is used as the stationary phase and a hydrophobic organic solvent or solvent system is used as the mobile phase, or conventional low pressure liquid chromatography (LPLC) systems.

SUMMARY OF THE INVENTION

It has now been discovered, however, that water-soluble chemiluminescent 1,2-dioxetane derivatives can be purified in high yields using modified HPLC, MPLC and LPLC systems. Specifically, it has been found that by subjecting impure water-soluble 1,2-dioxetane derivatives to conventional liquid chromatography techniques modified in the following manner:

(1) using a water-miscible organic solvent or solvent system in place of the customarily-used hydrophobic organic solvent or solvents;
(2) carrying out the purification at an alkaline pH above 7.0, and preferably above 8.0;
(3) neutralizing anionic 1,2-dioxetane derivatives with one or more alkali metal or quaternary ammonium counter cations;
(4) operating in the absence of organic or inorganic moieties containing unshared pairs of electrons, e.g., primary, secondary or tertiary amine groups, or excluding such moieties to as great an extent as can practicably be achieved; and (5) then desalting the thus-purified 1,2-dioxetanes by either the modified liquid chromatography method described above, but using pure water as the mobile phase, or by purifying and desalting the 1,2-dioxetanes in a single step, purified water-soluble chemiluminescent ,1,2-dioxetane derivatives which, as a consequence of their greater purity afford greater sensitivity in assays in which they are used to identify or quantify the presence, amount or structure of chemical or biological substances than do the unpurified dioxetanes, can be obtained in high yield, i.e., with minimal decomposition of the dioxetane being purified.

It is, therefore, an object of this invention to provide methods of purifying water-soluble chemiluminescent 1,2-dioxetane derivatives.

It is also an object of this invention to provide new liquid chromatography techniques for purifying water-soluble chemiluminescent 1,2-dioxetane derivatives.

Another object of this invention is to provide column packings suitable for the efficient, non-destructive purification of water-soluble, chemiluminescent 1,2-dioxetane derivatives by modified liquid chromatography techniques.

A further object of this invention is to provide mobile phases suitable for efficient, non-destructive purification of water-soluble chemiluminescent 1,2-dioxetane derivatives by modified liquid chromatography techniques.

A still further object of this invention is to provide means for desalting substantially pure, water-soluble 1,2-dioxetanes derivatives obtained by liquid chromatography techniques of this invention.

It is yet a further object of this invention to provide chemiluminescent, water-soluble derivatives of 1,2-dioxetanes produced in purified form by the methods of the invention.

These and other objects, as well as the nature, scope and utilization of this invention, will become readily apparent to those skilled in the art from the following description, the drawings and the appended claims.

BRIEF DESCRIPTION OF THE DRAWINGS

FIG. 1 shows the separation, by preparative HPLC chromatography on PLRP-S styrene-divinylbenzene copolymer particles as the stationary phase carried out in accordance with this invention, of the products of a synthesis of 3-(2'-spiroadamantane)-4-methoxy-4-(3''-phosphoryloxy)phenyl-1,2-dioxetane disodium salt ("AMPPD") from 3-(adamantylidenemethoxymethyl)-phenyl phosphate ("PEE") (FIG. (IV)).

FIG. 2 shows light emission from the reaction of the thus-purified AMPPD (FIG. 1) and its breakdown product (BP) with alkaline phosphatase.

FIG. 3A shows application, carried out in acordance with this invention, of preparative HPLC chromatography on PLRP-S resin to the separation of the products of AMPPD synthesis from PEE.

FIG. 3B shows analytical HPLC chromatography on PLRP-S resin of the AMPPD peak from FIG. 3A.

FIG. 3D shows analytical HPLC chromatography on PLRP-S resin of the desalted AMPPD from FIG. 3C.

FIG. 4 shows the application, carried out in acordance with this invention, of preparative HPLC chromatography on a silica-based reversed phase column (Dynamax C-18), using ammonium acetate-acetonitrile mobile phases, to the separation of the crude products from the synthesis of AMPPD from PEE (Fig. (IV)).

FIG. 6 shows analytical HPLC chromatography on a Dynamax C-18 column of AMPPD from FIG. 4 after overnight storage in ammonium acetate buffer, but without concentration by lyophilization.

FIG. 7 shows analytical HPLC chromatography on a Dynamax C-18 column of AMPPD from FIG. 4 after long-term storage in ammonium acetate buffer.

FIG. 8 shows application, carried out in acordance with this invention, of analytical HPLC chromatography on PLRP-S resin of 3-(2'-spiroadamantane)-4-methoxy-4-(3"-acetoxy)phenyl-1,2-dioxetane (AMAPD).

DETAILED DESCRIPTION OF THE INVENTION

Figure 9B:
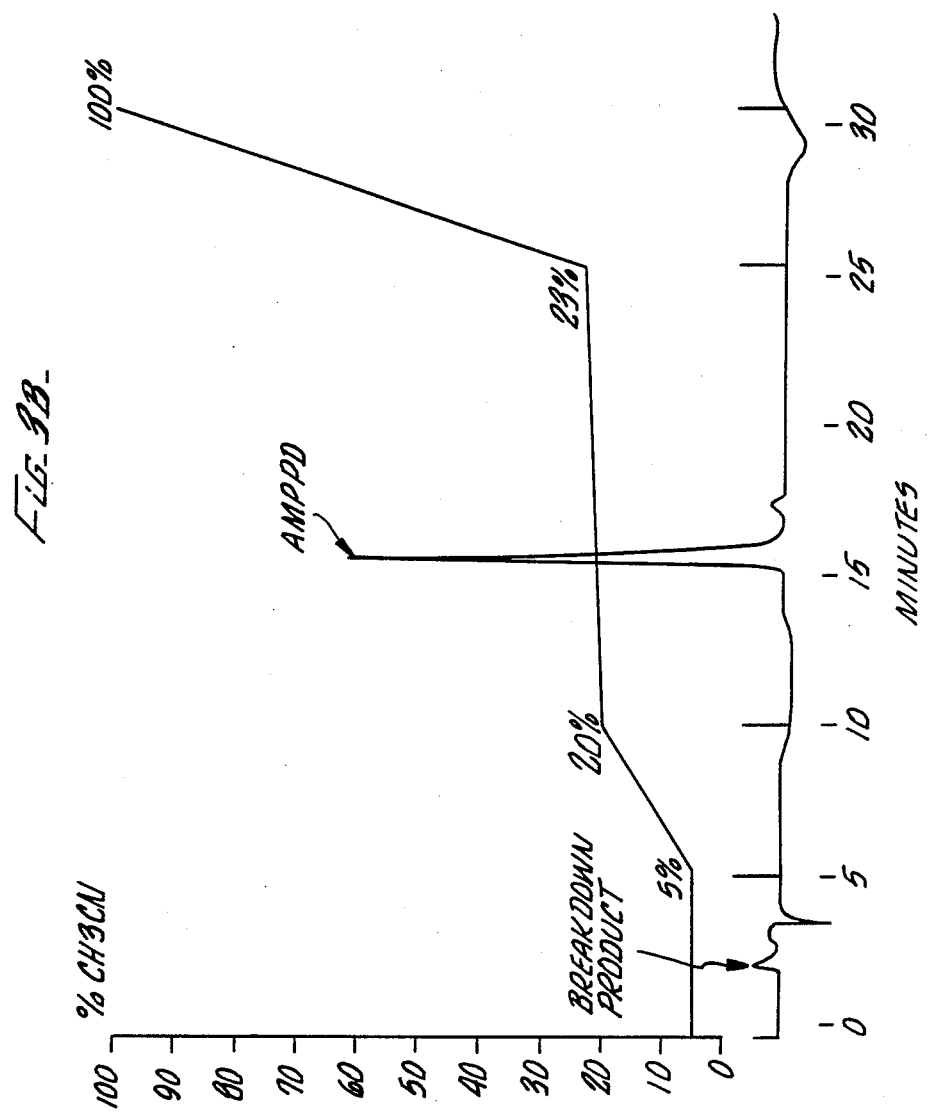
FIG. 9 shows sensitivity data for the chemiluminescent assay in the presence of HPLC purified (—■—) and crude (—□—) AMPPD.

The 1,2-dioxetanes, and in particular the enzymatically-cleavable dioxetanes, disclosed and claimed in the aforementioned copending Bronstein, Bronstein et al., Edwards et al. and Voyta et al. applications, and their thermally, chemically and electrochemically cleavable analogs, form one class of water soluble chemiluminescent 1,2-dioxetane compounds that can be purified by the method of this invention These 1,2-dioxetanes can be represented by the general formula:

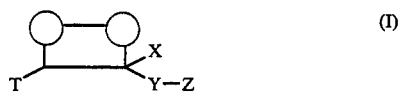

(I)

wherein T is an unsubstituted or substituted cycloalkyl, aryl, polyaryl or heteroatom group, e.g., an unsubstituted cycloalkyl group having from 6 to 12 ring carbon atoms, inclusive; a substituted cycloalkyl group having from 6 to 12 ring carbon atoms, inclusive, and having one or more substituents which can be an alkyl group having from 1 to 7 carbon atoms, inclusive, or a heteroatom group which can be an alkoxy group having from 1 to 12 carbon atoms, inclusive, such as methoxy or ethoxy, a substituted or unsubstituted aryloxy group, such as phenoxy or carboxyphenoxy, or an alkoxy group, such as methoxyethoxy or polyethyleneoxy, or a cycloalkylidene group bonded to the 3-carbon atom of the dioxetane ring in a spiro linkage, and having from 6 to 12 carbon atoms, inclusive, or a fused polycycloalkylidene group bonded to the 3-carbon of the dioxetane ring through a spiro linkage and having two or more fused rings, each having from 5 to 12 carbon atoms inclusive, e.g., an adamant-2-ylidene group.

The symbol X represents hydrogen or an alkyl, aryl, aralkyl, alkaryl, or heteroalkyl group having from 1 to 7 carbon atoms, inclusive; a straight or branched chain hydroxyalkyl group having from 1 to 7 carbon atoms, inclusive, or an —OR group in which R is a $C_1$-$C_{20}$ unbranched or branched, unsubstituted or substituted, saturated or unsaturated alkyl, cycloalkyl, cycloalkenyl, aryl, aralkyl or aralkenyl group, fused ring cycloalkyl, cycloalkenyl, aryl, aralkyl or aralkenyl group any of which may be fused to Y such that the emitting fragment contains a lactone ring, or an N,O or S hetero atom-containing group, or an enzyme-cleavable group containing a bond cleavable by an enzyme to yield an electron-rich moiety bonded to the dioxetane ring; preferably, X is a methoxy group.

The symbol Y represents a light-emitting fluorophore-forming group capable of absorbing energy to form an excited energy state from which it emits optically detectable energy to return to its original energy state.

The symbol Z represents hydrogen (in which case the dioxetane can be thermally cleaved by a rupture of the oxygen-oxygen bond), a chemically-cleavable group such as a hydroxyl group, an alkanoyl or aroyl ester group, or an alkyl or silyloxy group, or an enzyme-cleavable group containing a bond cleavable by an enzyme to yield a electron-rich moiety bonded to the dioxetane ring, e.g., a bond which, when cleaved, yields an oxygen anion, a sulfur anion or an nitrogen anion, and particularly an amido anion such as sulfonamido anion.

One or more of the substituents T, X and Z can also include a substituent which enhances the water solubility of the 1,2-dioxetane, such as a carboxylic acid, sulfonic acid, or their salts, or quaternary amino salt group and the appropriate counter ions; at least one of X and Z and preferably Z, is an enzyme-cleavable group and preferably an enzyme-cleavable phosphate ester group, and X and Y together can represent a fused fluorescent chromophore group bonded to the 4-carbon atom of the dioxetane through a spiro linkage, e.g., 6-disodium phosphoryloxy-2-oxa-1,2,3,4-tetrahydrophenanthra-1-ylidene group.

When using an enzymatically-cleavable 1,2-dioxetane, cleavage can be accomplished using an enzyme such as alkaline phosphatase that will cleave a bond in, for example, a Z substituent such as a phosphate ester group, to produce a Y anion and a charge transfer state that will, in turn, destabilize the dioxetane and cleave its oxygen-oxygen bond. Cleavage can also be accomplished by using an enzyme such as an oxido-reductase enzyme that will cleave the oxygen-oxygen bond directly; see the aforementioned Bronstein and Bronstein et al. copending U.S. patent applications.

Besides a phosphate ester group, Z in formula 1 above can be an enzyme-cleavable alkanoyloxy group, e.g., an acetate ester group, or an oxacarboxylate group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside group, β- D-glucoside group, α-D-mannoside group, β-D-mannoside group, β-D-fructofuranoside group, β-D-glucosiduronate group, p-toluene sulfonyl-L-arginine ester group, or p-toluene sulfonyl-L-arginine amide group.

Typical enzymatically-cleavable water-soluble chemiluminescent 1,2-dioxetanes for use in bioassays are the 3- (2'-spiroadamantane)-4-methoxy-4-(3"-phosphoryloxy)phenyl-1,2-dioxetane salts represented by the formula:

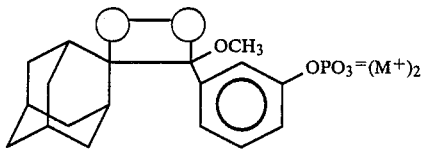

(II)

wherein M+ represents a cation such as an alkali metal, e.g. sodium or potassium, or a $C_1$-$C_{77}$ alkyl, aralkyl or aromatic quaternary ammonium cation, $N(R)_4^+$, in which each R can be alkyl, e.g., methyl or ethyl, aralkyl, e.g., benzyl, or form part of a heterocyclic ring system, e.g., pyridinium, and particularly the disodium salt.

Chemiluminescent water-soluble 1,2-dioxetane derivatives purifiable by the method of the present invention can be used when conducting immunoassays, such as those employed to detect biological analytes such as an enzyme or a member of a specific binding pair, e.g., an antigen-antibody pair, or a nucleic acid paired with a probe complementary to and capable of binding to all or a portion of the nucleic acid. Such assays include immunoassays used to detect a hormone such as $\beta$-human chorionic gonadotropin ($\beta$-HCG), thyroid stimulating hormone (TSH), follicle stimulating hormone (FSH), luteinizing hormone (LH) or the like, cell surface receptor assays, and nucleic acid assays used to detect viruses, e.g., HIV or HTLV III and cytomegalovirus, or bacteria, e.g., E. coli., and histocompatibility assays; for typical assay protocols see the working examples, infra, as well as the aforementioned Bronstein and Bronstein et al U.S. patent applications. These chemiluminescent dioxetanes can also be used in assays for a chemical analyte, such as potassium or sodium ions, or in assays for substances such as cholesterol or glucose in which the analyte is caused to decompose, for example, using an enzyme such as cholesterol oxidase or glucose oxidase, to form a substance, e.g., hydrogen peroxide, capable, in combination with another reagent, of causing the chemiluminescent compound to decompose.

Conventional HPLC and MPLC systems used to purify the products of organic chemical syntheses add to classic LPLC techniques the advantages of ease of operation, quick response, small sample volume, sensitivity, accuracy, precision and flexibility. Such conventional systems typically require the following components: a mobile phase, one or more pumps, an injector, a column, a stationary phase, a detector, a recorder and/or integrator for analytical purposes, and a collector for preparative purposes. In general, a sample of a substance to be purified is normally introduced into the system via an *injector* from which it is forced by a flowing stream of solvent called the *mobile phase* through a narrow bore transport tube to the *column*. The column is a tube (2-8 mm ID) containing small (5-125 μm) particles known as the *stationary phase* or *column packing* or *chromatographic bed*. The sample mixture separates as a result of different components adhering to or diffusing into the packing particles. Thus, once the mobile phase is forced through the chromatographic bed, a sample is separated into various zones of sample components. Ideally, each component will essentially migrate as a separate zone, often referred to as a band. The bands continue to migrate through the bed, and eventually pass out of the column (*elution*) and through any one of a number of *detectors*. The detector provides input into some recording device, such as a strip chart *recorder*: thus, a deflection of the pen of the recorder indicates the elution of one or more chromatographic bands. The recorder tracing from the elution of a single band is called a peak. The collection of peaks that results from an injected sample comprises the *chromatogrim* examples of which are found in Figure 1 -7, *infra*. Peaks are usually identified by their *retention time*, which is the time, in minutes, required to elute a band from the column.

In addition to conventional LPLC, which generally operates at atmospheric pressure, and HPLC, which operates at high pressures, chromatographic columns operated at intermediate pressures, i.e., MPLC, are also known in the art. All three general types of liquid chromatography are suitable for practicing this invention, when modified in accordance with this invention.

Five variables ar usually examined in order to achieve efficient separation and purification by liquid chromatography: column packing composition, composition of the mobile phase (i.e., solvent composition), column dimensions, mobile phase flow rate, and detector.

Packing materials should be held in a fixed configuration in order to function best as a chromatographic bed, and the particles should be relatively rigid in order to maintain this configuration under the pressures generated by forced flow of the mobile phase in HPLC and MPLC. Packings are categorized into 3 broad groups according to particle size and structure. Large particles, high capacity, fully porous packing are used predominately for HPLC and MPLC. High efficiency particles are used for analytical separations. Fully porous, high flow rate, high efficiency particles are used for both preparative and analytical separations.

Silica particles with cross-linked-SiOH functional groups are available commercially in both normal and reversed-phase forms. As shown in FIG. (III) below, in silica-based reversed phase particles, silica is capped with silyl groups containing various carbon-based constituents, R.

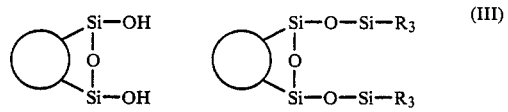

(III)

In order to avoid the instability in alkali of silica column packing materials, and to permit the separation of water-soluble 1,2-dioxetane derivatives at the alkaline pH values at which they are most stable, certain types of silica gel-based reversed phase resins or polymeric resins with reversed phase characteristics that are stable to elevated pH values are used in practicing this invention. Silica gel particles modified to contain hydrocarbons as R groups (Fig. (III)) and coated with a protective film that makes the silica stable to elevated pH values, are particularly useful in practicing this invention, such as Vydac ™ pH stable (2-10), TP104, $C_8$ to $C_{18}$ alkyl groups (Separations Group, Hesperia, CA).

Synthetic porous polymeric resins have also been shown to be effective adsorbents when used in conventional liquid chromatography techniques because of their stability to alkali, and can also be used in practicing this invention. Commonly employed resinous adsorbents of this type include relatively rigid, macroporous, crosslinked styrene-divinylbenzene copolymers, polyacrylates, including crosslinked polyacrylates, derivatized dextrans, and the like. Such adsorbents, and particularly the poly(styrene-divinylbenzene) adsorbents, can be used as column packings over a much wider pH range, typically 113, than can conventional alkyl group-functionalized silica gels without damage. In addition, such copolymeric particles, in contrast to silica-based prticles, are free of ionic sites on their surface. Copolymer particles of 5 to 10 μm diameter are preferred, with 10 μm particles being most preferred, for use in practicing this invention. Such copolymeric particles may be obtained from Polymer Laboratories Inc., Amherst, MA 01621 (PLRP-S 100 Å); the Hamilton Company, Reno, NV (PRP-1 beads 75 Å); Alltech Corp., Wilmington, Del. (RoGEL RP); and, Waters Associates Inc., Milford, Mass. 01757 (Styragel).

When using an LPLC separation technique in practicing this invention, materials analogous to the aforementioned HPLC and MPLC packings may be used. These include: the polystyrene/ divinylbenzene adsorbents usable in conventional HPLC and MPLC techniques, generally in larger particle sizes than can be used in regular liquid chromographic columns; e.g., Amberlite XAD-2 and XAD-4 poly(styrene-divinylbenzene) resins Rohm and Haas Co., Philadelphia, Penna.); polyacrylates, e.g., Amberlite XAD-7 porous polyacrylate beads (Rohm and Haas Co., Philadelphia, Penna.); and hydroxyalkoxypropyl dextrans containing from 10% to 50% by weight long chain alkyl ethers (from $C_{11}$ to $C_{18}$) (Pharmacia Fine Chemicals, Inc., Piscataway, N.J.).

A water-miscible solvent or solvent mixture is used as the mobile phase when practicing this invention. The solvent or solvent mixture may be used as such or admixed with buffer salts (preferably added as an aqueous solution) that are readily miscible in said solvent(s) and that will maintain the pH at values at which the 1,2-dioxetanes are most stable, i.e., above 7.0, preferably between 8.0 and 9.0. Where aqueous solutions of buffer salts are admixed with the solvents, it is necessary to select buffer pairs that not only exhibit good buffering capacity at the desired pH value, but also ones whose removal will not have a destructive effect on the purified dioxetanes. Sodium or potassium salts or mixed sodium/potassium salts of carbonic, phosphoric, boric or diethylbarbituric acids, which have pKa values in the useful range (i.e., above 6.7) are preferred buffers in carrying out this invention, with carbonic acid salt buffers being most useful. Although several amines, e.g., the weak base tris(hydroxylmethyl)aminomethane, have pKb values in the useful range, and exhibit good buffering capacity above pH 7.0, for reasons discussed above, primary, secondary or tertiary amine-containing buffers cannot be used as they will lead to destruction of the 1,2-dioxetane derivatives of the invention either during concentration by lyophilization or during long storage in the presence of such buffers.

When purifying and desalting charged dioxetanes by the one-step method, the mobile phase, which consists of the water-miscible organic solvent admixed with pure water, is brought to the requisite alkaline pH by titrating the anionic groups with alkali metal or quaternary ammonium counter cations. The salt of the dioxetane derivative serves to buffer the dioxetane during the combined purification/desalting procedure.

When purifying charged dioxetanes (see, e.g., FIG. (II) above), the nature of the counter cation will also influence the resolution of the compounds during chromatography. For example, the disodium salt of the dioxetane derivative shown in Fig. (II) above is resolved from impurities better than is the corresponding sodium/ammonium salt.

Solvents useful in practicing this invention can be selected by reference to standard classifications of the solvent properties of common liquids (see, e.g., Snyder, L., *J. Chrom*. 92:223 –30 (1974)) or from solvent water-miscibility tables such as that found in the J. T. Baker Co. catalog. When silica particles not bonded to functional R groups are used as the stationary phase (FIG. (III)), one uses a nonpolar mobile phase across a polar support —the packing polarity is high, the solvent polarity is low to medium, the sample elution order is least polar-first, and increasing solvent polarity reduces elution time. When using bonded-silica and copolymers as the adsorbents, one uses a polar mobile phase across a nonpolar support —the packing polarity is low, the solvent polarity is medium to high, the order of sample elution is most polar-first, and increasing solvent polarity decreases elution time.

When practicing this invention using as column packings functional R group-bonded ph-stabilized silicas, styrene/ divinylbenzene copolymer resins and their derivatives, polyacrylate beads and their derivatives, or alkylether or quaternary amino alkyl dextrans, acetonitrile-water mixtures containing sodium bicarbonate buffers are particularly suitable as the mobile phase. A mobile phase preferred for dissolving a sample for injection into a liquid chromatography column is 5% acetonitrile in 0.1 % (w/v) aqueous sodium bicarbonate buffer (pH 8.6). Under certain circumstances the sample may be dissolved in 100% aqueous solutions for injections. Thus, for example, when the analytical column is packed with Polymer Science Inc's. PLRP-S, poly(styrene-divinylbenzine) resin, 100Å, having the dimensions 8 μm, 15 cm ×4.6 mm, and the preparative column also contains PLRP-S resin, 100Å, having the dimensions 10 μm, 300 cm ×25 mm, the preferred mobile phase is 0.1% (w/v) sodium bicarbonate buffer, pH 8.6, with an acetonitrile gradient (5% to 100%). As noted above and as will be demonstrated in examples below, primary, secondary and tertiary amine salt buffers are unsuitable when practicing this invention.

Other solvents with broad water-miscibility properties (see the Snyder and J. T. Baker publications, supra) similar to those of acetonitrile are also suitable, e.g., straight or branched chain alkanols containing from 1 to 6 carbon atoms, inclusive, such as methanol, ethanol, n-propanol, isopropanol, n-butanol, hexanol, and the like, aliphatic ketones containing from 3 to 5 carbon atoms, such as acetone, methyl ethyl ketone, diethyl ketone, and the like, cyclic ethers such as tetrahydrofuran, dioxane, and the like, N,N-dialkyl formamides such as N,N-dimethylformamide, and the like, N,N-dialkylacetamides such as N, N-dimethylacetamide, and the like, dimethylsulfoxide, and the like, as well as mixtures thereof with acetonitrile, with each other and with the co-solvents.

The chromatographic column dimensions, and the temperature, flow rates and time of chromatographic separations of the 1,2-dioxetanes of the invention are not critical, and are based primarily upon the requirements for efficient chromatography.

The liquid chromatography systems of the invention may be used in either preparative or analytical modes. Preparative columns require a larger load capacity, and typically are 25 mm O.D.×300 cm long. In contrast, analytical columns are smaller, typically 4 mm O.D.×15 cm long. Those skilled in the art of chromatography will, without undue experimentation, select chromatographic bed dimensions appropriate to the amounts of materials being separated.

Flow rates of mobile phases are adjusted based upon four major factors: (1) the dimensions of the chromatographic bed; (2) the degree of peak resolution desired; (3) the particle size of the stationary phase; and (4) the time required to get satisfactory peak resolution. For example, analytical columns use slower flow rates, typically 0.1–5 ml./minute, whereas preparative columns use faster flow rates, typically 10 to several hundred ml./minute. Typically, a HPLC run is complete within 30 minutes, while LPLC separations may take several hours, and MPLC intermediate times. The times required for chromatographic runs are not critical to the practice of this invention.

Temperatures for HPLC separation are typically 20°–30° C., i.e., at room temperature or slightly above, whereas useful temperatures for the MPLC and LPLC range from 0° C. to room temperature.

Following concentration of a reaction mixture from the chemical syntheses of a chemiluminescent water-soluble 1,2-dioxetane derivative, several impurities may be present in the concentrate or residue. These may include water-insoluble matter which is removable from an aqueous solution by filtration, for example, through a 0.4μ pore-size membrane filter. Other impurities may include unreacted precursor and degradation products. For example, in the syntheses of 3-(2'-spiroadamantane)-4-methoxy-4-(3''-phosphoryloxy)-phenyl-1,2-dioxetane ("AMPPD") from 3-(adamantylidenamethoxymethyl) phenylphosphate ("PEE"), there may be present as impurities unreacted PEE plus degradation products adamantanone and a 3-phosphoryloxybenzoate ("Breakdown Product") (Fig. (IV)), as well as photolytic by-products from sensitizers used in the synthesis, e.g., Rose Bengal and Methylene Blue.

The eluted, substantially pure 1,2-dioxetane derivatives obtained by practicing this invention can preferably be desalted in the following manner. The dioxetane peak is collected, frozen and lyophilized (freeze-dried), then dissolved in water and injected into the same type of HPLC, MPLC or LPLC chromatography column used in the purification step. Alternatively, the dioxetane peak is collected, diluted with pure water and chromatographed directly without lyophilization. The dioxetane is then eluted with a gradient of a suitable water-miscible organic solvent in pure water; salt buffers are, of course, not used in desalting procedures. The range of the water-miscible organic solvent(s) in water is 0 to 100%, preferably 5 to 100%. The concentration limits of the gradients are determined by the following two factors: (1) the concentration of organic solvent necessary to elute the desired product from the adsorbent; an (2) the requirement that the organic solvent be completely miscible and exist in a single phase at the concentration required to elute the desired product. Those skilled in the art of liquid chromatography will, without undue experimentation, be able to determine the steepness and concentration rang of the organic solvent gradient. The major peak which is collected, frozen, and lyophilized for storage or use will be substantially salt-free.

The desalting step may also be accomplished using molecular sieve columns suitable for small molecules such as, Bio-Gel P-2 (Bio-Rad Corp., Richmond, Calif.), and the like.

Where little or no precursor for the photolytic step in the synthesis of the 1,2-dioxetane derivative is present (see, for example, FIG. (IV)), i.e., less than 3% as determined by an analytical chromatogram generated by a Knauer Variable Wavelength Detector (Rainin Instrument Co., Woburn, Mass.,) operating at 270 nm, purification and desalting may be accomplished in a single chromatographic procedure. The reaction product is concentrated, the residue is taken up in pure water or an organic solvent-water mixture, sufficient alkali metal or quaternary ammonium salt is added to bring the pH to about 8.6, insoluble matter is filtered off, and the product purified and desalted by single column chromatography using a gradient of an organic solvent in pure water as the mobile phase.

The degree of purity of the water-soluble 1,2-dioxetane derivatives obtained when practicing this invention can be determined by one or more art-recognized methods. One such method simply involves the examination of detector-produced analytical chromatographs following preparative purification of the 1,2-dioxetane derivative by liquid chromatography. Where peaks representing impurities, i.e., precursor and breakdown products (see FIG. (IV)), are absent or slight when compared to the peak produced by the desired product, the product is substantially pure.

Another such method involves testing the 1,2-dioxetane derivative as a substrate for an enzyme in a chemiluminescence assay (see for example, Example 2 infra), and comparing its behavior to that of an authentic sample of highly pure substrate in the same assay. The light intensity produced per unit amount of the substrate is directly proportional to the degree of purity of the substrate, when compared to the light intensity produced by the highly pure sample. When the light intensity produced from pure and impure substrate is plotted as a function of the molar concentration of the biochemical analyte, a family of parallel sigmoid curves is produced; this is called a sensitivity plot. The sensitivity curve for an impure sample will be shifted to the right of the curve for a pure sample; that is, the assay is less sensitive when using the impure sample. The greater the degree of impurity, the greater the shift of the sensitivity curve to the right. Purification of the crude reaction products of the chemical syntheses of the chemiluminescent, water-soluble 1,2 dioxetane derivatives by the methods of this invention will increase the sensitivity of the assay using the dioxetane product by at least 2-fold, preferably about 10-fold (see Example 6, FIG. 9).

Yet another test method is based upon the behavior of the starting material used to prepare the 1,2-dioxetane derivative and its breakdown product(s) (e.g., PEE and Breakdown Product (FIG. (IV)) as a competitive inhibitor of the interaction of the 1,2-dioxetane itself (e.g., AMPPD) with an enzyme (e.g., alkaline phosphatase) in a chemiluminescence assay. A double reciprocal plot (Lineweaver-Burk plot) of the velocity of the reaction as a function of 1,2-dioxetane concentration, in the absence and presence of contaminating starting material or breakdown product(s), will produce a family of straight line curves that will not only identify the type of inhibition (competitive, noncompetitive or mixed), but will also provide an estimate of the degree of contamination.

In order that those skilled in the art can more fully understand this invention, the following examples are set forth. These examples are given solely for illustrative purposes, and should not be considered as expressing limitations unless so set forth in the appended claims.

EXAMPLE 1

PREPARATIVE ISOLATION OF AMPPD BY HPLC

Following synthesis of AMPPD FIG.(IV)), solvent was removed from the crude mixture, the residue was dissolved in 0.1% $NaHCO_3$ buffer, pH 8.6, and filtered through a 0.4 micron nylon filter to remove insoluble materials. Thereafter, 14 ml (140 mg) of the crude product were injected into a preparative reversed phase PLRP-S (Polymer Science, Inc.) column, 100 Å, 10 μm particle size, column dimensions 300 cm × 25 mm. The mobile phase, 0.1% $NaHCO_3$ buffer, pH 8.6, in an acetonitrile gradient, was pumped through the column at a flow rate of 10ml/min. Detection was by a UV monitor at a wave length of 270 nm; the chart speed was 1 cm/min.

The chromatogram is shown in FIG. 1. The step-gradient of acetonitrile in 0.1% $NaHO_3$ buffer is shown on an ordinate. The desired product, substantially pure disodium AMPPD, is shown as the major peak at the elution of 9 minutes. AMPPD was well separated from a breakdown product eluting earlier at 3 minutes. Trace amounts of the phosphorylated enol ether (PEE) intermediate in AMPPD synthesis is shown as a minor peak on the trailing edge (10-11 minutes). Methods for the synthesis of AMPPD are provided in copending U.S. patent application Nos. 889,823 and 140,197, the latter now abandoned, which are incorporated herein to the extent that they disclose synthetic routes to water-soluble chemiluminescent 1,2-dioxetane derivatives.

EXAMPLE 2

IDENTIFICATION OF PEAKS ON FIG. 1

The breakdown product and the AMPPD from FIG. 1 were collected, dried by lyophilization, then tested as a substrate for alkaline phosphatase in a chemiluminescence assay. The details of this assay are provided in copending U S. Pat. Application Ser. No. 889,823, which is incorporated herein by reference to the extent that it discloses assay conditions for alkaline phosphatase. Light emission was determined in a Turner 20E Luminometer.

The upper tracing of FIG. 2 shows the light emission following reaction of alkaline phosphatase with the compound eluting at 9 minutes (FIG. 1). The light emission was typical of AMPPD. In contrast, there was no light emission upon reaction of alkaline phosphatase with the compound of the 3-minute peak (lower tracing), demonstrating that peak 3 material is not chemiluminescent, and is the Breakdown Product shown below in FIG. (IV).

A second product of the thermal destruction of AMPPD is adamantanone (FIG.(IV)). This compound exhibits no UV absorbancy, and, therefore, it does not appear in the chromatogram. However, as adamantanone is produced in a 1:1 molar ratio with Breakdown Product, the amount of Breakdown Product on a chromatogram is a close approximation of the amount of adamantanone present.

The PEE, AMPPD and Breakdown Product of FIG. (IV) may all exist as the monobasic or dibasic salt.

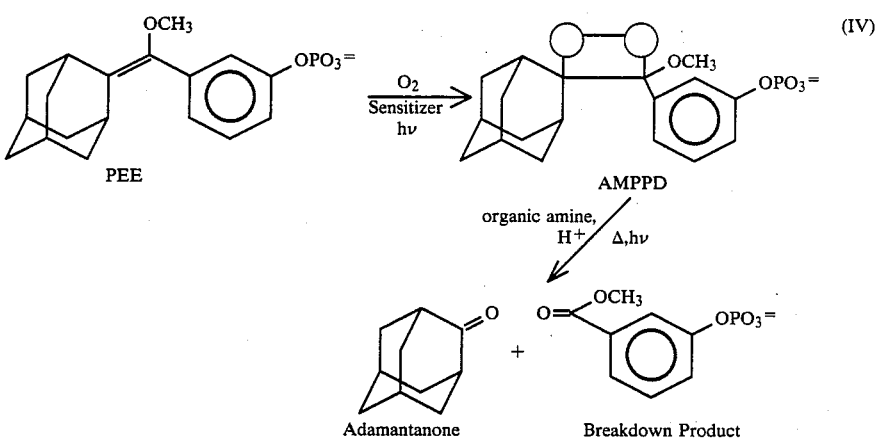

EXAMPLE 3

PREPARATIVE ISOLATION AND DESALTING OF AMPPD BY HPLC

Two ml. (20 mg) of a crude mixture of AMPPD, PEE and breakdown product (FIG.(IV)) were chromatographed on a preparative scale (300 cm × 25 mm) reversed phase PLRP-S column. The mobile phase was a gradient of acetonitrile in 0.1 % $NaHCO_3$, pH 8.6, at a flow rate of 20 ml/min. Elution of peaks was monitored at 270 nm, at a strip chart speed of 5 mm/min.

As shown in the strip chart tracing of FIG. 3A, the AMPPD peak (17-19 minutes) was sharply separated from the intermediate PEE peak (20 minutes) and broadly separated from the Breakdown Product peak (4 minutes).

The AMPPD peak from FIG. 3A was freeze-dried to concentrate the product, dissolved in 0.1% $NaHCO_3$ buffer, pH 8.6, then injected into an analytical scale reversed phase PLRP-S column (100 Å, 8 μm, 15 cm × 4.6 mm). As before, the mobile phase was a gradient of acetonitrile in 0.1% $NaHCO_3$ buffer, pH 8.6. The strip chart tracing shown in FIG. 3B shows that essentially only a single peak, that of AMPPD, was obtained (position 16 on the abscissa). This result demonstrated that the initial preparative HPLC run had produced substantially pure AMPPD.

Several preparative AMPPD fractions were combined and desalted by chromatography on a preparative PLRP-S column. The sample size was 230 ml. containing 140 mg of AMPPD. The mobile phase was a 5–60% gradient of acetonitrile in water. The very large amount of AMPPD loaded into the column eluted as a broad peak between positions 20 and 30 (14% to 26% acetonitrile gradient in water). In other experiments not detailed here, it was discovered that the presence of a salt buffer at pH values above 7 is required in order to elute AMPPD as a narrow band. As also shown in the strip chart tracing of FIG. 3C, the AMPPD band completely separated from colored contaminants that eluted at higher acetonitrile concentrations.

Figure 3C:
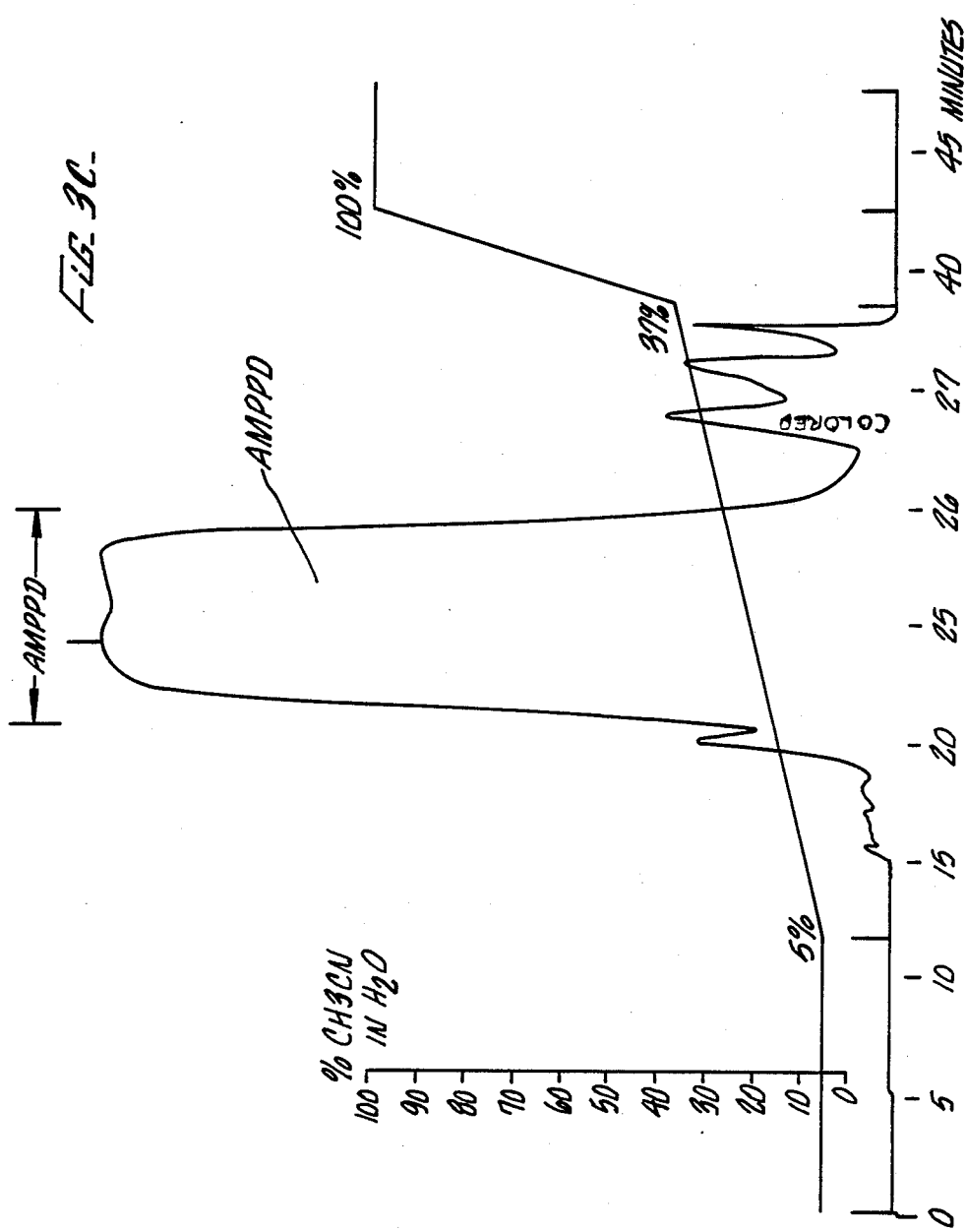
FIG. 3C shows desalting of the AMPPD peak from FIG. 3A by preparative HPLC chromatography on PLRP-S resin.

Peak fractions from FIG. 3C were combined, lyophilized, then analyzed by analytical HPLC on a reversed phase PLRP-S analytical column with a gradient of acetonitrile in 0.1% $NaHCO_3$ buffer, pH 8.6, as the mobile phase. As shown in FIG. 3D, analytical HPLC chromatography demonstrated that the previously-desalted AMPPD was substantially pure. This demonstrates that both desalted and non-desalted AMPPD preparations are stable for long periods in water.

EXAMPLE 4

PURIFICATION OF AMPPD BY SILICA-BASED REVERSED PHASE HPLC IN AMMONIUM SALT BUFFER

A crude mixture of products from the synthesis of AMPPD from PEE (FIG. (IV)) was fractionated on an analytical size HPLC column of Dynamax C-18 particles, a silica-based reversed phase packing. The mobile phase was a gradient of acetonitrile in 0.1% ammonium acetate buffer, pH 7.0. Elution of peaks was monitored at 270 nm, at a chart speed of 5 mm/min. As shown in the strip chart tracing of FIG. 4, the AMPPD peak (5–6 minutes) was sharply separated from earlier-eluting contaminants (2–4 minutes), but not separated well from trailing edge contaminants (6–8 minutes).

Figure 5:
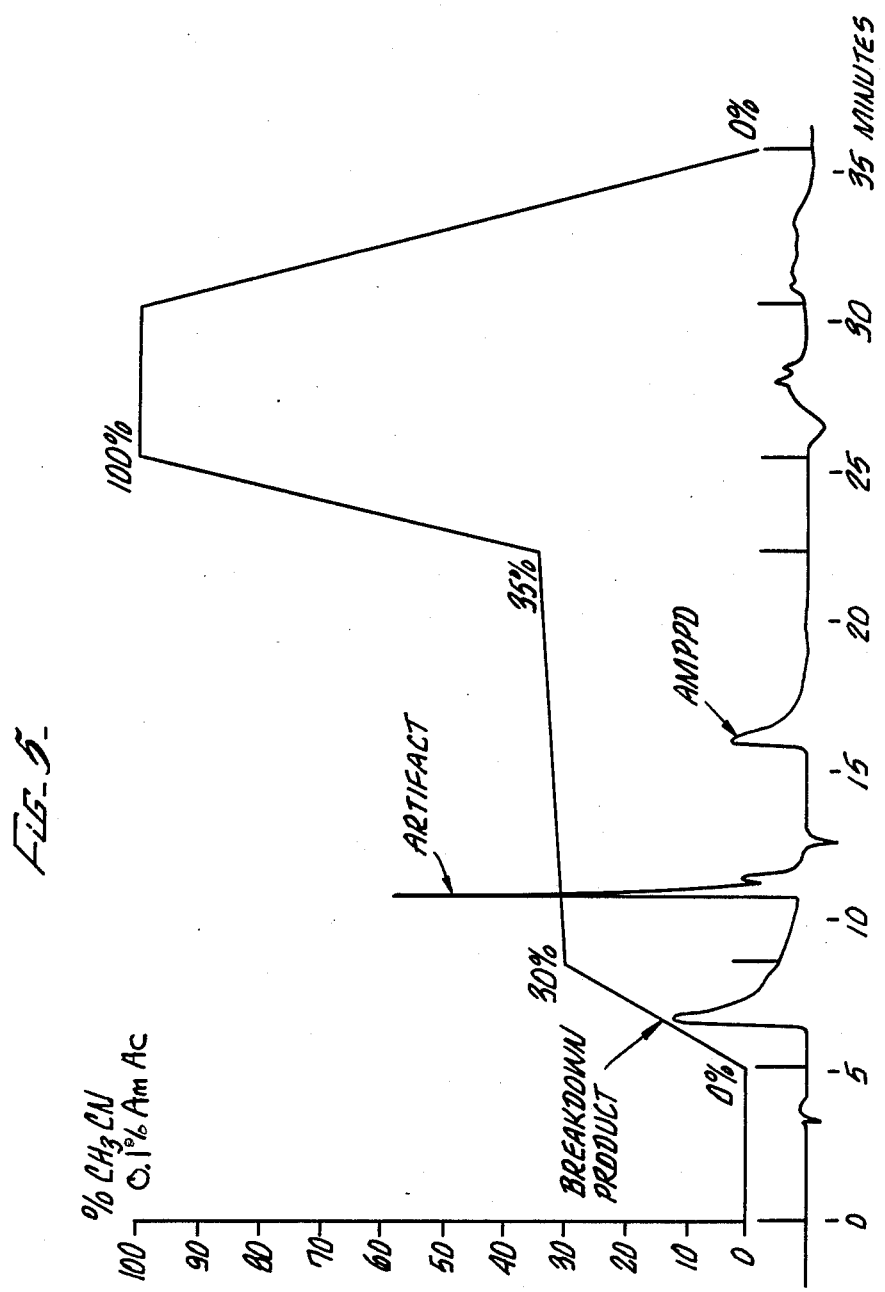
FIG. 5 shows analytical HPLC chromatography on a Dynamax C-18 column of AMPPD from FIG. 4 after lyophilization in the presence of $NH_4^{30}$ ions.

The AMPPD fraction from FIG. 4 was collected, freeze-dried, then fractionated on an analytical size column of Dynamax C-18 using as the mobile phase a gradient of acetonitrile in 0.1% ammonium acetate, pH 7.0. The strip chart tracing of FIG. 5 showed extensive production of breakdown product (7–8 min retention time) at the expense of AMPPD (16–17 min. retention time). This demonstrates that AMPPD is unstable in the presence of concentrated ammonium ions.

Short term storage of AMPPD in ammonium acetate buffer (i.e., without concentration by lyophilization) did not decompose AMPPD. The 6 minute AMPPD peak from FIG. 4, which eluted with 31% acetonitrile in 0.1% ammonium acetate buffer, pH 7.0, was stored overnight in this solution without concentration, then chromatographed by HPLC on an analytical Dynamax C-18 column in a gradient of acetonitrile in 0.1% ammonium acetate buffer, pH 7.0 (FIG. 6). Brief (overnight) storage of AMPPD in the presence of ammonium acetate did not lead to significant breakdown of this dioxetane derivative.

When, however, AMPPD in the 6-minute peak from preparative HPLC (FIG. 4) was stored in the presence of the ammonium acetate column effluent for long periods of time at 4° C. (in the dark), analytical HPLC on Dynamax $C_{18}$ demonstrated increased breakdown of AMPPD (FIG. 7).

While applicant does not wish to be bound by any proposed mechanism for the destructive effect of $NH_4+$ on acid-labile 1,2-dioxetanes, several mechanisms can be proposed. The electron pair of ammonia produced from $NH_4+$ during concentration by lyophilization or long storage may induce decomposition of 1,2-dioxetane derivatives. Alternatively, the $NH_4+$ cation in the buffer may exchange with the alkali metal cation of the AMPPD, which could subsequently produce an unstable protonated dioxetane upon lyophilization. In addition to the $NH_4+$ effects, acetate-containing buffers may become acidic during concentration and thereby decompose the 1,2-dioxetanes.

EXAMPLE 5

PURIFICATION OF 3-(2'-SPIROADAMANTANE)-4-METHOXY-4-(3"-ACETOXY) PHENYL-1,2-DIOXETANE (AMAPD) BY HPLC

Following chemical synthesis of AMAPD, the crude mixture was filtered as in Example 1, then chromatographed on an analytical PLRP-S (Polymer Science, Inc.) column, 100 Å, 8 μm particle size, column dimensions 6.5 ×150 mm O.D. The mobile phase, 0.1% $NaHC_3$ buffer, pH 8.6, in a 60 to 100% acetonitrile gradient was pumped through the column at a flow rate of 3 ml/min. Detection was by a UV monitor at a wavelength of 270 nm.

The chromatogram is shown in FIG. 8. Substantially pure AMAPD eluted as a single peak at about 6 minutes at about 78% acetonitrile. Contaminants all eluted prior to the institution of the acetonitrile gradient, i.e., prior to 1.40 min. Methods for the syntheses of AMAPD are provided in copending U.S. patent application No. 140,197, now abandoned, which is incorporated herein to the extent that it discloses synthetic routes to AMAPD.

EXAMPLE 6

DETERMINATION OF PURITY OF AMPPD BY A SENSITIVITY PLOT

The alkaline phosphatase chemiluminescent assay was applied to a relatively crude sample of AMPPD from Example 4, FIG. 5, and to an HPLC purified sample of AMPPD from Example 3, FIG. 3D. Light intensity produced in the chemiluminescent assay was plotted as a function of the molar concentration of alkaline phosphatase in the assay mixture (FIG. 9).

The data revealed that the sensitivity of the purified AMPPD was at least an order of magnitude greater than that of the crude AMPPD, and that this difference in sensitivity was exhibited at all concentrations of alkaline phosphatase.

With purified AMPPD, alkaline phosphatase could be detected at concentrations as low as about $10^{-15}$ M.

We claim:

1. A purified chemiluminescent water-soluble derivative of 1,2-dioxetane prepared by a method comprising subjecting the corresponding impure 1,2-dioxetane derivative, as an alkali metal or quaternary ammonium salt, at an alkaline pH, to liquid chromatography on an alkali-stable stationary phase having the chromatographic characteristics of a reversed phase absorbent, using a mobile phase comprising at least one water-miscible organic solvent for the 1,2-dioxetane derivative, the method being carried out at a concentration of organic or inorganic moieties containing unshared pairs of electrons as low as can practically be achieved.

2. A purified chemiluminescent water-soluble derivative of 1,2-dioxetane prepared as recited in claim 1, wherein the liquid chromatography is high pressure liquid chromatography.

3. A purified chemiluminescent water-soluble derivative of 1,2-dioxetane prepared as recited in claim 1, wherein said the liquid chromatography is medium pressure liquid chromatography.

4. A purified chemiluminescent water-soluble derivative of 1,2-dioxetane prepared as recited in claim 1, wherein the liquid chromatography is low pressure liquid chromatography.

5. A purified chemiluminescent water-soluble derivative of 1,2-dioxetane prepared as recited in claim 1, wherein the mobile phase is a 0% to 100% gradient of a water-miscible organic solvent in an aqueous buffer.

6. A purified chemiluminescent, water-soluble derivative 1,2-dioxetane as recited in claim 5 wherein the buffer is a salt/weak acid buffer pair of pH greater than about 7.0 selected from the group consisting of carbonate, phosphate, borate and diethylbarbiturate buffers.

7. A purified chemiluminescent water-soluble derivative of 1,2-dioxetane prepared as recited in claim 1, wherein the mobile phase is a 0% to 100% gradient of a water-miscible organic solvent in pure water.

8. A purified chemiluminescent water-soluble derivative of 1,2-dioxetane prepared as recited in claim 1, wherein the water miscible solvent is selected from the group consisting of acetonitrile, aliphatic ketones containing from 3 to 5 carbon atoms, straight or branched chain alkanols containing from 1 to 6 carbon atoms, alkylated sulfoxides, cyclic ethers, N,N-dialkyformamides and N,N-dialkyacetamides.

9. A purified chemiluminescent water-soluble derivative of 1,2-dioxetane prepared as recited in claim 1, wherein the stationary phase is a silica-based composition stable to pH values of about 7.0 or greater.

10. A purified chemiluminescent, water-soluble derivative of 1,2-dioxetane prepared as recited in claim 9, wherein silica is bonded to a hydrocarbon composition.

11. A purified chemiluminescent, water-soluble derivative of 1 2-dioxetane prepared as recited in claim 10, wherein the hydrocarbon composition comprises a compound having an alkyl group of from 8 to 18 carbon atoms in length.

12. A purified chemiluminescent water-soluble derivative of 1,2-dioxetane prepared as recited in claim 10 wherein the hydrocarbon composition comprises an aromatic hydrocarbon.

13. A purified chemiluminescent water-soluble derivative of 1,2-dioxetane prepared as recited in claim 9, wherein silica is bonded to quaternary aminoalkyl groups.

14. A purified chemiluminescent water-soluble derivative of 1,2-dioxetane prepared as recited in claim 1, wherein the stationary phase is a copolymer of styrene and divinylbenzene.

15. A purified chemiluminescent water-soluble derivative of 1,2-dioxetane prepared as recited in claim 1, wherein the stationary phase is a polyacrylate.

16. A purified chemiluminescent water-soluble derivative of 1,2-dioxetane prepared as recited in claim 1, wherein the stationary phase is an alkylether dextran or a quaternary aminoalkyl dextran.

17. A purified chemiluminescent water-soluble derivative of 1,2-dioxetane prepared by first chromatographically purifying an impure 1,2-dioxetane derivative by the method recited in any one of claims 28-43, inclusive, then desalting the thus-obtained purified 1,2-dioxetane derivative by a method comprising lyophilizing the chromatographic eluate fraction containing the purified 1,2-dioxetane derivative at low temperatures in vacuo to produce a dry powder; dissolving the dry powder in water or a water-miscible organic solvent to from an aqueous solution of an alkali metal or quaternary ammonium salt of said 1,2-dioxetane derivative; and, fractionating the 1,2-dioxetane derivative salt solution by a chromatographic means wherein the mobile phase is used in the absence of added salts.

18. A purified chemiluminescent water-soluble 1,2-dioxetane derivative prepared as recited in claim 17, wherein during the desalting step the 1,2-dioxetane derivative is fractionized by a chromatographic means selected from the group consisting of high pressure liquid chromatography, medium pressure liquid chromatography, normal pressure chromatography, and molecular sieve chromatography.

19. A purified chemiluminescent water-soluble derivative of 1,2-dioxetane prepared by first chromatographically purifying an impure 1,2-dioxetane derivative by the method recited in any one of claims 28-43, inclusive, then desalting the thus-obtained purified 1,2-dioxetane derivative by a method comprising diluting a chromatographic fraction containing the purified, eluted, 1,2-dioxetane derivative by chromatographic means wherein the mobile phase is used in the absence of added salts.

20. A purified chemiluminescent water-soluble 1,2-dioxetane derivative prepared as recited in claim 19 wherein during the desalting step the 1,2-dioxetane derivative is fractionated by a chromatographic means selected from the group consisting of high pressure liquid chromatography, medium pressure liquid chromatography, normal pressure liquid chromatography, and molecular sieve chromatography.

21. A purified chemiluminescent water-soluble derivative of 1,2-dioxetane prepared by a method comprising purifying and desalting the corresponding impure 1,2-dioxetane derivative by concentrating the impure 1,2-dioxetane derivative, diluting the concentrated solution of 1,2-dioxetane derivative in pure water or an organic solvent-water mixture, according to the thus-prepared solution sufficient alkali metal or quaternary ammonium salt to bring the pH to above 7.0, filtering off insoluble matter, and chromatographing the filtered solution using as the mobile phase a gradient of an organic solvent in pure water.

22. A purified chemiluminescent water-soluble derivative of 1,2-dioxetane prepared as recited in claim 21, wherein the filtered solution is chromatographed by a chromatographic means selected from the group consisting of high pressure liquid chromatography, medium pressure liquid chromatography and normal pressure liquid chromatography.

23. A purified chemiluminescent water-soluble derivative of 1,2-dioxetane prepared as recited in any one of claims 1-16, 21 or 22, inclusive, having the general structure:

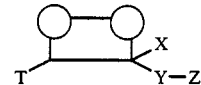

where in T is an unsubstituted or substituted cycloalkyl group or a fused cycloalkylidene or polycycloalkylidene group bonded to the dioxetane ring through a spiro linkage; X is hydrogen or an alkyl, aryl, aralkyl, alkaryl, heteroalkyl, heteroaryl, cycloalkyl or cyloheteroalkyl group, or an —OR wherein R is a $C_1-C_{20}$ unbranched or branched, unsubstituted or substituted, saturated or unsaturated alkyl, cycloalkyl, cycloalkenyl, aryl, aralkyl or aralkenyl group, fused-ring cycloalkyl, cycloalkenyl, aryl, aralkyl or alkenyl group that may be fused to Y to form a lactone ring, or an N, O or S-heteroatom-containing group, or an enzyme-cleavable group containing a bond cleavable by an enzyme to yield an electron-rich moiety bonded to the dioxetane ring; Y is a fluoroescent chromophore-forming group capable of absorbing energy to form an excited energy state from which it emits optically-detectable energy to return to its original energy state; Z is hydrogen, a hydroxyl group or an enzyme-cleavable group containing a bond cleavable by an enzyme to yield an electron-rich moiety bonded to the dioxetane ring, at least one of X and Z being an enzyme-cleavable group; and T, X and Z can also include a substituent that enhances the water-solubility of the 1,2-dioxetane.

24. The purified chemiluminescent water-soluble 1,2-dioxetane derivative of claim 23 which is a 3-(2'-spiroadamantane)-4-methoxy-4-(3''-phosphoryloxy)-phenyl-1,2-dioxetane salt represented by the formula

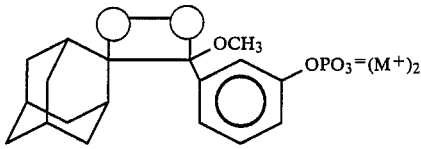

wherein $M^+$ represents a cation which is an alkali metal, a $C_1-C_7$ alkyl, aralkyl or aromatic quaternary ammonium cation, $N(R)_4^+$, in which each R can be alkyl, aralkyl, or can form part of a heterocyclic ring system.

25. The purified chemiluminescent water-soluble 1,2-dioxetane derivative of claim 24 wherein $M^+$ is sodium.

26. A purified chemiluminescent water-soluble 1,2-dioxetane derivative prepared as recited in claim 17, having the general structure:

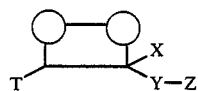

wherein T is an unsubstituted or substituted cycloalkyl group or a fused cycloalkylidene or polycycloalkylidene group bonded to the dioxetane ring through a spiro linkage; X is hydrogen or an alkyl, aryl, aralkyl, alkaryl, heteroalkyl, heteroaryl, cycloalkyl or cycloheteroalkyl group, or an —OR wherein R is a $C_1-C_{20}$ unbranched or branched, unsubstituted or substituted, saturated or unsaturated alkyl, cycloalkyl, cycloalkenyl, aryl, aralkyl or aralkenyl group, fused-ring cycloalkyl, cycloalkenyl, aryl, aralkyl or alkenyl group that may be fused to Y to form a lactone ring, or an N, O or S-heteroatom-containing group, or an enzyme-cleavable group containing a bond cleavable by an enzyme to yield an electron-rich moiety bonded to the dioxetane ring; Y is a fluorescent chromophore-forming group capable of absorbing energy to form an excited energy state from which it emits optically-detectable energy to return to tis original energy state; Z is hydrogen, a hydroxyl group or an enzyme-cleavable group containing a bond cleavable by an enzyme to yield an electron-rich moiety bonded to the dioxetane ring, at least one of X and Z being an enzyme-cleavable group; and T, X and Z can also include a substituent that enhances the water-solubility of the 1,2-dioxetane.

27. The purified chemiluminescent water-soluble 1,2-dioxetane derivative of claim 26 which is a 3-(2'-spiroadamantane)-4-methoxy-4-(3''-phosphoryloxy)-phenyl-1,2-dioxetane salt represented by the formula

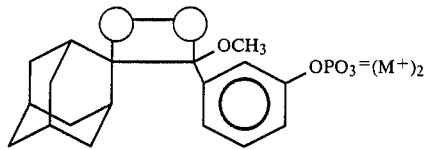

wherein $M^+$ represents a cation which is an alkali metal, a $C_1-C_7$ alkyl, aralkyl or aromatic quaternary ammonium cation, $N(R)_4^+$, in which each R can be alkyl, aralkyl, or can form part of a heterocyclic ring system.

28. The purified 1,2-dioxetane derivative of claim 27, wherein $M^{30}$ is sodium.

29. A purified chemiluminescent water-soluble derivative of 1,2-dioxetane prepared as recited in claim 19 having the general structure:

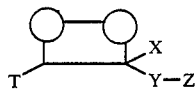

wherein T is an unsubstituted or substituted cycloalkyl group or a fused cycloalkylidene or polycycloalkylidene group bonded to the dioxetane ring through a spiro linkage; X is hydrogen or an alkyl, aryl, aralkyl, heteroalkyl, heteroaryl, cycloalkyl or cycloheteroalkyl group, or an —OR wherein R is a $C_1-C_{20}$ unbranched or branched, unsubstituted or substituted, saturated or unsaturated alkyl, cycloalkyl, cycloalkenyl, aryl, aralkyl or aralkenyl group, fused-ring cycloalkyl, cycloalkenyl, aryl, aralkyl or alkenyl group that may be fused to Y to form a lactone ring, or an N, O or S-heteroatom-containing group, or an enzyme-cleavable group containing a bond cleavable by an enzyme to yield an electron-rich moiety bonded to the dioxetane ring; Y is a fluorescent chromophore-forming group capable of absorbing energy to form an excited state from which it emits optically-detectable energy to return to its original energy state; Z is hydrogen, a hydroxyl group or an enzyme-cleavable group containing a bond cleavable by an enzyme to yield an electron-rich moiety bonded to the dioxetane ring, at least one of X and Z being an enzyme-cleavable group and T, Y and Z can also include a substituent that enhances the water-solubility of the 1,2-dioxetane.

30. The purified chemiluminescent water-soluble 1,2-dioxetane derivative of claim 29 which is a 3-(2'-spiroadamantane)-4-methoxy-4-(3''-phosphoryloxy)-phenyl-1,2-dioxetane salt represented by the formula

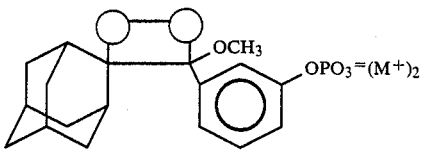

wherein $M^+$ represents a cation which is an alkali metal, a $C_1-C_7$ alkyl, aralkyl or aromatic quaternary ammonium cation, $N(R)_4^+$, in which each R can be alkyl, aralkyl, or can form part of a heterocyclic ring system.

31. The purified chemiluminescent water-soluble 1,2-dioxetane derivative of claim 30 wherein $M^+$ is sodium.

* * * * *